Figure 1:
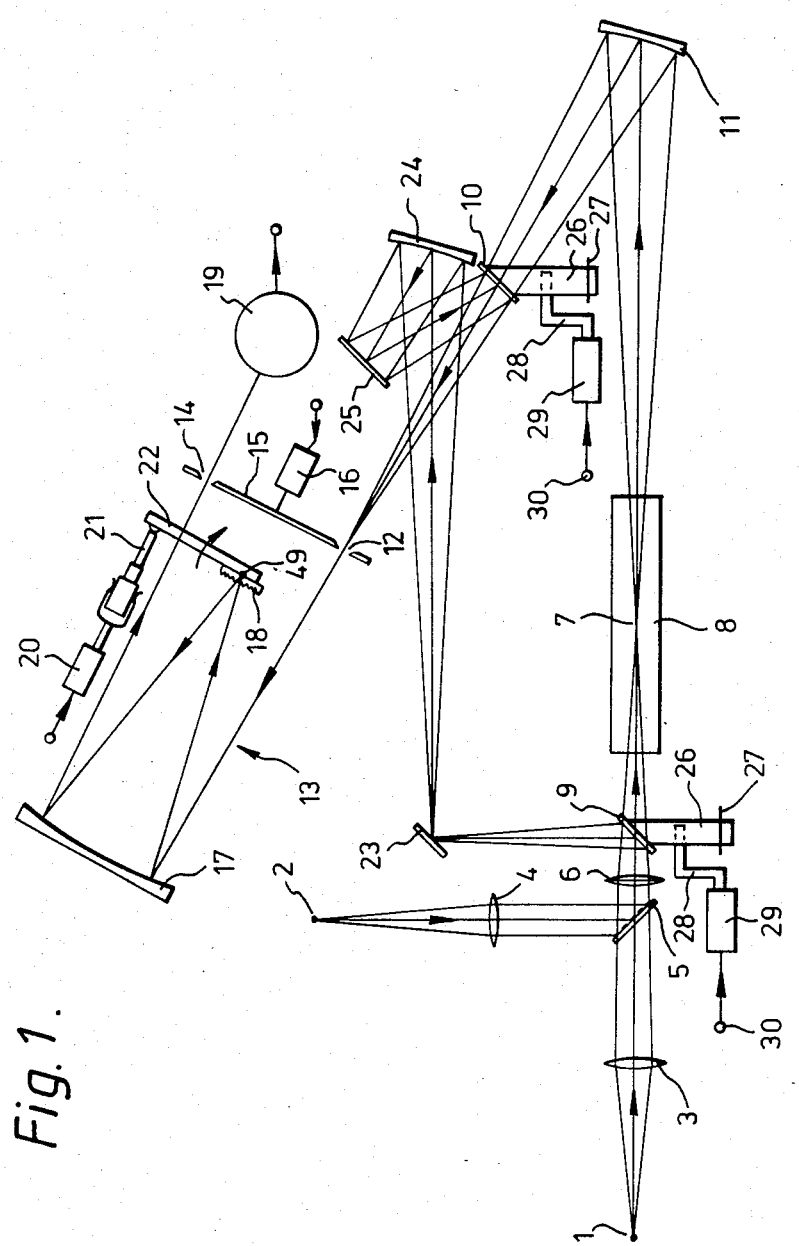

United States Patent [19]

Stockdale

[11] Patent Number: 4,508,451
[45] Date of Patent: Apr. 2, 1985

[54] ATOMIC ABSORPTION SPECTROPHOTOMETER

[75] Inventor: Trevor J. Stockdale, Cambridge, England

[73] Assignee: U.S. Philips Corporation, New York, N.Y.

[21] Appl. No.: 450,489

[22] Filed: Dec. 16, 1982

[30] Foreign Application Priority Data

Jan. 19, 1982 [GB] United Kingdom ............... 8201371

[51] Int. Cl.³ .......................... G01J 3/42; G01N 21/72
[52] U.S. Cl. ............................... 356/315; 356/325
[58] Field of Search ............... 356/315, 319, 323, 325, 356/417

[56] References Cited

U.S. PATENT DOCUMENTS 4,238,830 12/1980 Unvala .......................... 356/326

OTHER PUBLICATIONS

Mills, Laboratory Equipment Digest, vol. 14, No. 10, Oct. 1976, pp. 97,99,101,103,105.

*Primary Examiner*—F. L. Evans
*Attorney, Agent, or Firm*—Paul R. Miller

[57] ABSTRACT

In atomic absorption spectrophotometer, a reference path may be provided for radiation which excludes the flame. This radiation provides a signal from a detector which varies only with the instrumental drift produced by variations in the radiation source brightness and by variations in detector gain. The signal can be used to compensate for drift in other signals received through a sample path including the flame. In the present invention, radiation passes through the sample path continuously during measurement, and only through the reference path between sample measurements. Movable mirrors shift the radiation between the paths upon externally applied commands. Conveniently, the reference path measurement is made while the flame is stabilized during the change between samples. The reference path measurements are stored and used to correct for drift.

13 Claims, 4 Drawing Figures

ATOMIC ABSORPTION SPECTROPHOTOMETER

This invention relates to a double-path atomic absorption spectrophotometer including sample and reference paths for resonance line radiation characteristic of an atomic element from a source of the radiation to a detector with the sample path including the flame and the reference path excluding the flame, and signal processing means responsive to the output of the detector and to command signals such that when a command signal indicates required measurement of a blank sample the signal processing means responds to the detector output from the sample path for a given sample measurement time to set a baseline therein, such that repeated and compared measurements of the detector output from the reference path are used by the signal processing means to update said baseline, and such that when a said command signal indicates required measurement of a sample to be analysed, the signal processing means responds to the detector output from the sample path for a given sample measurement time to quantitatively determine the atomic element in the sample to be analysed with respect to the updated baseline.

An atomic absorption spectrophotometer having such a "double beam (or path) in time" arrangement is known in which the means for alternatively providing the sample and reference paths includes a chopper mirror, two symmetrically arranged sets of fixed mirrors providing respective paths from the chopper mirror through and around the flame and a fixed recombiner mirror. The chopper mirror is continuously rotated by a motor at a speed such that the resonance line radiation from the source is regularly and alternately, typically at 20 ms intervals determined by the frequency of the mains power supply to the motor, directed along the two paths at all times including during the sample measurement times. This known "double beam, or path, in time" arrangement achieves its purpose of enabling the signal processing means to update the baseline so as to correct for instrumental drift which is mainly due to variation with time in the intensity of the resonance line radiation emitted by the source and in the response to the detector. However, the interruption of the sample path during the sample measurement times reduces the energy of the radiation reaching the detector during those times which adversely affects the signal-to-noise ratio for the sample measurements and hence the detection limit of the atomic element in a sample being analysed.

An object of the invention is to overcome the above-mentioned disadvantage of the known arrangement.

This invention is based on an appreciation that the above-described known "double beam in time" arrangement retains features which are derived from and essential to a "double beam in time" arrangement used in ultra-violet/visible ratio recording wavelength scanning spectrophotometers, but which are not essential to its use in flame atomic absorption spectrophotometer. In such ultra-violet/visible instruments a blank sample and a sample to be analysed are simultaneously and continuously present while a chopper mirror alternately directs radiation into two symmetrically arranged paths, that is a reference path through the blank sample and a sample path through the sample to be analysed. The ratio of the intensity of radiation received by a detector from the paths containing these two samples is repeatedly measured, at a rate determined by the speed of the chopper mirror, while the wavelength of the radiation is scanned. The symmetrical arrangement of the two paths and the fast repeated ratio measurement from the two paths are necessary for a scanning instrument. In a flame atomic absorption spectrophotometer a blank sample must be present in the flame in the sample path to enable a baseline to be set, it must at a later time be replaced in the flame in the sample path by a sample to be analysed with radiation at an unchanged single wavelength, and the reference path avoiding the flame is used for the purpose of correcting for instrumental drift. It is now appreciated that drift correction can be satisfactorily achieved by repeated and compared measurements from the reference path being made at times near to but not within the times during which measurements are made from the sample path, and furthermore it is not necessary for the two paths to be symmetric.

According to the invention there is provided an atomic absorption spectrophotometer as described in the opening paragraph of this specification, characterised in that control means for determining the periods for which the sample and reference paths are provided are responsive to command signals such that the sample path is provided uninterrupted for the whole of each sample measurement time.

The control means may be responsive to the command signals to provide the reference path for a period near to each sample measurement time. This will be sufficient to provide satisfactory drift correction.

In a spectrophotometer as described in the previous paragraph, each period for which the reference path is provided may be before the respective sample measurement time and sampling means may be responsive to the command signals to aspirate the respective sample to the flame atomiser during each period for which the reference path is provided. Before a sample measurement time can commence, an appreciable time, usually several seconds, is required for the aspirated sample to first reach the flame and then for atomisation of the sample in the flame to stabilise. In most cases the time required for making a measurement from the reference path will be short enough for it to be completed during this aspiration time prior to stabilisation, and so the provision of drift correction in this way will have substantially no effect on the total time taken to analyse one or more samples for an atomic element.

In a spectrophotometer as described in the penultimate or the previous paragraph, responsive to the command signal indicating required measurement of a blank sample in the sample path the signal processing means may derive and store a first digital value representing the baseline and a second digital value representing the detector output from the reference path, each further time the reference path is provided in an operation to analyse one or more samples for the atomic element the signal processing means deriving a further digital value representing the detector output from the reference path and comparing the further digital value with the second digital value in order to update the first digital value. Holding the second digital value stored for the duration of an operation to analyse one or more samples enables efficient signal processing to update the baseline.

In a spectrophotometer according to the invention, the means for alternatively providing the sample and reference paths may include two mirrors each movable under control of the control means between a first and a second position, in which first position the radiation does not impinge on the movable mirrors so that the sample path is provided, and in which second position the radiation impinges on the two movable mirrors in the line of the sample path respectively before and after the flame and on intervening fixed mirrors so that the reference path is provided, the sample and reference paths being asymmetric by virtue of the movable and fixed mirrors which are present only in the reference path. This optical arrangement including two movable mirrors can be conveniently and simply controlled by the control means for determining the periods for which the sample and reference paths are provided. The asymmetric arrangement of the sample and reference paths does not have the disadvantages in an atomic absorption spectrophotometer that it would have in a wavelength scanning instrument and moreover it facilitates an arrangement of the sample path for low optical energy loss of the resonance line radiation reaching the detector.

In a spectrophotometer as described in the previous paragraph, the radiation will be focussed at the flame position in the sample path but may not be focussed at the second positions of the movable mirrors. In the above-mentioned known "double beam in time" arrangement using a continuously rotating chopper mirror to direct the resonance radiation alternately along the sample and reference paths several times per second, the radiation must be focussed at the position of the chopper mirror to provide a small cross-section beam which is quickly traversed by the chopper mirror. In a spectrophotometer according to the invention the path along which the resonance radiation is directed may be changed only once every several seconds and so it is acceptable for the movable mirrors to slowly traverse a large cross-section, that is to say unfocussed, beam. This facilitates a further simplification of the arrangement of the sample path for low optical energy loss of the resonance line radiation reaching the detector.

Figure 2:
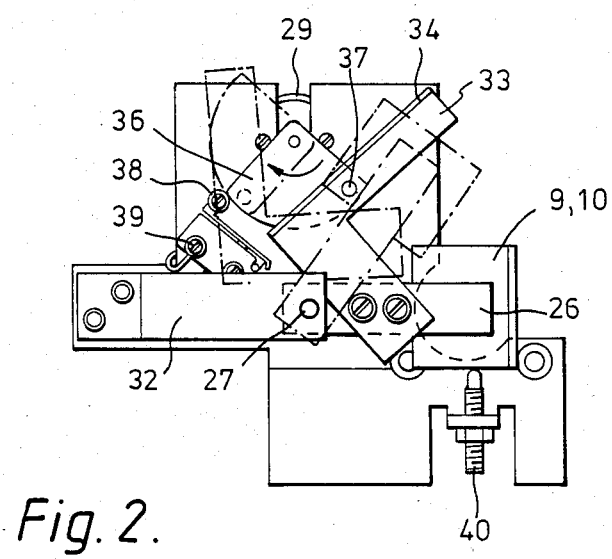
Figure 3:
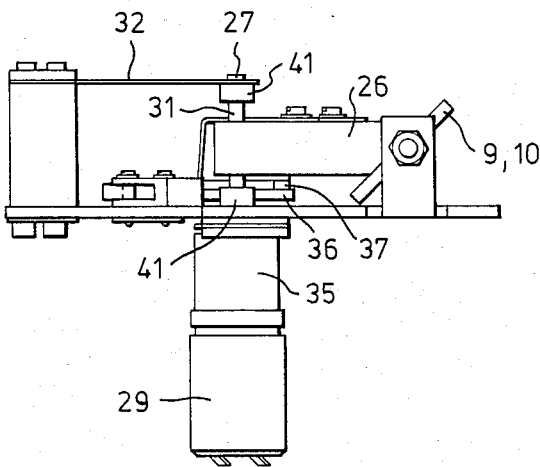
Figure 4:
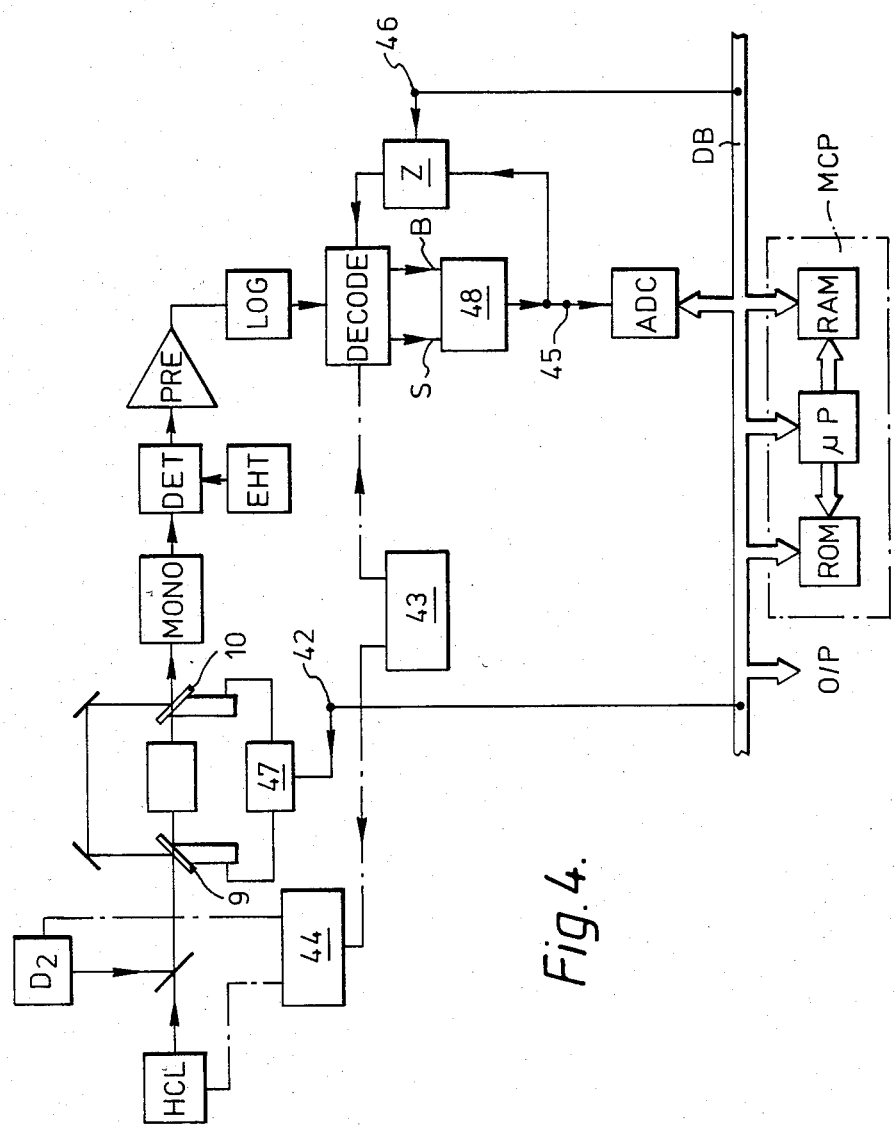

The invention will now be described in more detail with reference to the accompanying drawing(s) in which:

FIG. 1 shows schematically, the optical system of a spectrophotometer according to the invention, FIGS. 2 and 3 show two views of a mechanism for moving the mirrors used to deflect the beam into the reference path, and FIG. 4 shows a control system for the spectrophotometer of FIG. 1.

Referring to FIG. 1, a source 1 provides resonance line radiation characteristic of an atomic element to be detected and measured. Source 1 may be a hollow cathode lamp (HCL), or an electrodeless discharge lamp (EDL), each containing a quantity of the element. Background source 2 provides radiation which is substantially constant as a function of wavelength over the pass band to be used. Typically, source 2 is a deuterium filled hollow cathode lamp.

Lenses 3 and 4 provide approximately collimated beams, from the sources, impinging upon a "speckled" beam combining mirror 5. This mirror comprises a transparent substrate onto which a metal mirror has been evaporated via a mask having an array of apertures such that the total aperture area equals the remaining mask area. Thus, the intensities of both beams are halved and the beams are superposed. Lens 6 images both sources onto the center 7 of the flame above burner 8, which flame rises normal to the plane of the drawing.

The sample path will first be described and for this purpose, the movable mirrors 9 and 10 are presumed to have been moved out of the radiation paths by mechanisms to be described later. The flame center 7 is imaged by the off-axis spherical mirror 11 at unity magnification onto the entrance slit 12 of monochromator 13. Up to slit 12 the beams are shown as cones of rays but within the monochromator only the chief ray of the beam is shown for clarity. The entrance slit 12 and the exit slit 14 are mounted upon a disc 15 which may be rotated by a motor 16 to bring any one pair of a number of pairs of diametrically opposite slits, covering a range of slit widths, into operation. The monochromator 13 is of Ebert design in which the slit plate is in the focal plane of a spherical mirror 17. Thus, the beam is collimated by mirror 17 and reflected onto the reflective diffraction grating 18 where it is dispersed and reflected back to mirror 17. The beam is then refocussed onto the exit slit 14 through which it passes to the detector 19 which is a side-window photomultiplier tube shown end-on. The grating lines are normal to the plane of the drawing. The grating is rotatable about an axis 49 normal to the drawing and is driven by a stepping motor 20, via a micrometer 21 and a sine bar 22, to bring light of the desired wavelength onto the exit-slit.

The reference path is obtained when the mirrors 9 and 10 are in the position shown in FIG. 1. The superposed and convergent beams are then brought to a focus at a fixed mirror 23 which is comparatively small in area since the beam diameter is small at this point. The point of reflection at mirror 23 then corresponds to the flame center 7. The mirror 23 is set to reflect the chief ray of the beam parallel to the chief ray through the flame. An off-axis spherical mirror 24 of the same focal length as mirror 11 is placed at the same distance from mirror 23 as point 7 is from mirror 11 and at the same orientation as mirror 11. Thus, the magnification and the off-axis aberrations of the two spherical mirrors are the same. Fixed mirror 25 and movable mirror 10 then bring the beam back onto the sample path so that it is again focussed on the entrance slit 12.

It is a virtue of this optical layout that, when the sample path is in use, there is only one optical component, spherical mirror 11, between the flame and the monochromator entrance slit 12, thus minimising the sample beam intensity reduction by absorption at mirror surfaces. The presence of four additional mirror surfaces in the reference path is not a disadvantage since flame noise is absent and the gain of the photomultiplier can be increased to provide an adequate reference signal.

In FIG. 1 the movable mirrors 9 and 10 are shown schematically mounted upon an arm 26 pivoted about an axis 27 parallel to the plane of the drawing. A crank 28 driven by a motor 29 is shown schematically lifting arm 26 and mirror 9 or 10 out of the beam in response to an input command 30.

In practice it is necessary to register mirrors 9 and 10 in positions about axis 27 repeatable to some 2 seconds of arc to ensure the constancy of the reference beam signal. FIG. 2 shows a beam axis view of a mechanism for providing mirror movement with this desired accuracy of settled mirror position. FIG. 3 shows a view of this mechanism from below the mirror 9 or 10. The mirror movement axis 27 is provided by a shaft 31 having tungsten carbide balls at each end bearing upon Ringstones 41, one of which is spring loaded against the shaft 31 by leaf spring 32. Arm 26 comprises a rigidly attached member 33 having a ledge 34. A quadrant cam 36, having a peg 37 near one end of the quadrant, is drivable in clockwise rotation by motor 29 via a reduction gearbox 35. The peg 37 engages the underside of ledge 34. The roller 38 of microswitch 39 is contacted by the end of the quadrant cam remote from peg 37 when the mirror is in the down position intercepting the beam. In the down position the peg 37 is clear of ledge 34 and the bottom edge of the mirror glass rests, under gravity, upon an adjustable end stop. Thus, in the down position, the settled mirror position is kinematically defined. In the down position, cam 36 closes microswitch 39 which provides a stop signal for the motor. When it is required to lift the mirror out of the beam, switch 39 is overridden by external control and the motor is energised. The peg then engages the ledge and lifts arm 26 until the cam releases switch 39 which again provides a stop of motor motion. When it is required to lower the mirror into the beam the motor is again energised by external control and clockwise motion of the cam is restored. As the mirror 9 approaches the stop 40, the direction of motion of the peg 37 becomes more closely parallel to the ledge 34, slowing down the rate of descent of the mirror so that it finally engages the stop gently. The cam continues to move until switch 39 is contacted, carrying peg 37 clear of ledge 34 to ensure that kinematic definition of the mirror position is obtained.

The advantages of a spectrophotometer in which a reference path for radiation clear of the flame can be provided at will for the HCL and deuterium lamps by the above described optical system, rather than repetitively at a constant rate throughout the sample measurement time, will now be described in relation to FIG. 4.

FIG. 4 shows the element and background sources in a highly schematic form of the optical system. A movable mirror control input is shown at 42, which, on command, will move the mirrors 9, 10 to provide the sample or reference paths. The monochromator (MONO) and photomultiplier detector (DET) are shown schematically. A pre-amplifier (PRE) is shown which converts the current output of the photomultiplier into a low impedance output voltage source suitable for feeding a unit (LOG) which provides a voltage output proportional to the logarithm of its input. As is common practice in spectrophotometers, the element and background sources are each repetitively pulsed, for example at 150 Hz, but at different times. In this example the HCL lamp is pulsed for 3.3 ms followed by the $D_2$ lamp for 1.0 ms, followed by a period of 2.0 ms when both lamps are off. In FIG. 4, unit 43 provides master timing pulses by frequency tripling from the mains frequency. These pulses are fed to the lamp supply unit 44 and to a decoder (DECODE) which uses the timing pulses to separate the LOG pulses into two separate channels. The LOG pulses in each channel are converted, by sample-and-hold circuits within the decoder, into two d.c. signals, S and B, for the sample and background channels respectively. Subtraction of the B signal from the S signal in subtractor 48 provides a background corrected absorbance output signal at 45.

In a zero setting operation prior to measuring the absorbance of a sample containing the element, a blank sample is aspirated into the flame. Using the sample path, the S-B output at 45 is fed back by unit Z under command from input 46 as a gain adjustment control signal to the background channel in the decoder to servo the S-B output to zero. The background channel gain so obtained is maintained when standard samples or unknown samples containing the metal are aspirated into the flame for measurement. This zero setting operation therefore establishes an instrumental baseline.

Such background corrected absorbance values still need to be corrected for instrumental drift, that is, the baseline must be updated to account for drift. The two main causes of such drift are change in output of the light sources HCL and D2, and change in gain of the photomultiplier detector DET. The effect of drift is to cause an apparent change in measured absorbance value at signal 45 at a rate which, throughout a working period of several hours, may change in value and in sign, but which over a period of not more than a few minutes is substantially constant. It is the essence of the present invention that it is only necessary to interrupt the sample path at intervals of a few minutes or less, and only for a few seconds at each interruption, to make measurements of the apparent absorbance change. If radiation from the source drifting in output is incident upon the detector drifting in gain, via a reference path excluding the flame, the change in absorbance signal 45 between consecutive reference measurements divided by the time between the measurements gives a drift rate expressed as an apparent absorbance change per second which can be used to correct for long term drift.

During the sample measurement time, which in practice may vary from a few seconds to 100 seconds, the sample path through the flame is uninterrupted providing an improved amount of resonance line radiation in the flame and hence improving the signal to noise ratio at the detector. The efficiency of the instrument is also improved by recognizing that when changing from one sample to another, it takes 6 seconds typically for the conditions in the flame to stabilise. During this time no effective sample measurement can be made and the reference path measurement for drift correction can conveniently be made at this time. In an automated spectrophotometer, a succession of blank samples, standard samples of known concentration of the element and of samples of unknown concentration are aspirated in turn and absorbance values noted. A reference path measurement can therefore conveniently be made between samples.

It will be clear that for the full benefit of the invention to be obtained, particularly in an automated spectrophotometer, a number of events in the instrument should be under command signals from a central source and that the drift calculations and the concentration calculations made from the standard and unknown absorbance values would be best made in an automatic calculator. A microprocessor MCP is a suitable device for both these purposes and is shown schematically in FIG. 4. The microprocessor comprises a central processor $\mu P$, read only memory, ROM, containing instructions and fixed data, and a random access memory, RAM, for receiving input data from and outputting data to a data bus DB. The absorbance values at 45 are digitised in an analogue-to-digital converter ADC whence they are input to RAM via DB. The results of calculations are output to a display or printer at O/P.

The ROM contains timing instructions for establishing the reference path. Via input 42, mirror motor control unit 47 receives commands from the MCP at times which determine the periods for which the sample and reference paths are provided. The microprocessor also contains stored commands for initiating a blank aspiration and for simultaneously initiating the zero-setting or baseline-setting operation via input 46 to unit Z.

When measurements are made via the reference path for updating the baseline to compensate for drift, either the HCL lamp alone or the HCL lamp and the background lamp, $D_2$ in the example, may be used as the radiation source.

I claim:

1. An atomic absorption spectrophotometer comprising
   a flame atomizer,
   means for alternatively providing sample and reference paths,
   said sample path including said flame atomizer, and said reference path excluding said flame atomizer,
   detector means for detecting resonance line radiation characteristics of atomic elements,
   circuitry means for providing command signals representative of control of the spectrophotometer,
   signal processing means for processing signals from said detector means and for processing said command signals,
   wherein when one of said command signals indicates a required measurement of a blank sample, said signal processing means responds to an output signal from said detector means, said output signal being representative of said sample path for a given measurement time to set a baseline,
   wherein said detector means provides repeated and compared measurements from said reference path to update said baseline in said signal processing means, and
   wherein when one of said command signals indicates a required measurement of a sample to be analyzed, said signal processing means responds to a detector output representative of said sample path for a given sample measurement time to quantitatively determine at least one atomic element of said sample to be analyzed with respect to the updated baseline, and
   control means for determining periods for which said sample and reference paths are provided, said control means being responsive to said command signals,
   such that said sample path is provided uninterrupted for the entire period of each sample measurement time.

2. A spectrophotometer according to claim 1, wherein said control means provide said reference path for a period near to each sample measurement time.

3. A spectrophotometer according to claim 2, wherein said reference path is provided before respective sample measurement times, and wherein sample means responsive to said command signals are provided for aspirating a respective one of said samples to said flame atomizer during each reference path period.

4. A spectrophotometer according to claim 3, wherein said signal processing means derives and stores a first digital signal representing said baseline and a second digital signal representing outputs of said detector means from said reference path in response to one of said command signals indicating required measurement of one of said blank samples, and wherein during each further time said reference path is provided with an operation to analyze at least one sample for atomic elements, said signal processing means derives a further digital value representing the output of said detector means from said reference path, said signal processing means comparing said further digital value to said second digital signal in order to update said first digital signal.

5. A spectrophotometer according to claim 4, wherein said means for alternatively providing said sample and reference paths includes two movable mirrors, said two mirrors each being movable under control of said control means between a first position and a second position, wherein in said first position radiation does not impinge on said two movable mirrors to form said sample path, and wherein in said second position said radiation impinges on said two movable mirrors and on intervening fixed mirrors to form said reference path, said sample and reference paths being asymmetric by said movable and fixed mirrors being present only in said reference path.

6. A spectrophotometer according to claim 5, wherein said radiation is focussed in said flame atomizer in said sample path but is not focussed at a movable mirror in said reference path.

7. A spectrophotometer according to claim 3, wherein said means for alternatively providing said sample and reference paths includes two movable mirrors, said two mirrors each being movable under control of said control means between a first position and a second position, wherein in said first position radiation does not impinge on said two movable mirrors to form said sample path, and wherein in said second position said radiation impinges on said two movable mirrors and on intervening fixed mirrors to form said reference path, said sample and reference paths being asymmetric by said movable and fixed mirrors being present only in said reference path.

8. A spectrophotometer according to claim 7, wherein said radiation is focussed in said flame atomizer in said sample path but is not focussed at a movable mirror in said reference path.

9. A spectrophotometer according to claim 2, wherein said signal processing means derives and stores a first digital signal representing said baseline and a second digital signal representing outputs of said detector means from said reference path in response to one of said command signals indicating required measurement of one of said blank samples, and wherein during each further time said reference path is provided with an operation to analyze at least one sample for atomic elements, said signal processing means derives a further digital value representing the output of said detector means from said reference path, said signal processing means comparing said further digital value to said second digital signal in order to update said first digital signal.

10. A spectrophotometer according to claim 2, wherein said means for alternatively providing said sample and reference paths includes two movable mirrors, said two mirrors each being movable under control of said control means between a first position and a second position, wherein in said first position radiation does not impinge on said two movable mirrors to form said sample path, and wherein in said second position said radiation impinges on said two movable mirrors and on intervening fixed mirrors to form said reference path, said sample and reference paths being asymmetric by said movable and fixed mirrors being present only in said reference path.

11. A spectrophotometer according to claim 10, wherein said radiation is focussed in said flame atomizer in said sample path but is not focussed at a movable mirror in said reference path.

12. A spectrophotometer according to claim 1, wherein said means for alternatively providing said sample and reference paths includes two movable mirrors, said two mirrors each being movable under control of said control means between a first position and a second position, wherein in said first position radiation does not impinge on said two movable mirrors to form said sample path, and wherein in said second position said radiation impinges on said two movable mirrors and on intervening fixed mirrors to form said reference path, said sample and reference paths being asymmetric by said movable and fixed mirrors being present only in said reference path.

13. A spectrophotometer according to claim 12, wherein said radiation is focussed in said flame atomizer in said sample path but is not focussed at a movable mirror in said reference path.

* * * * *